(12) United States Patent
Matheny

(10) Patent No.: US 8,778,012 B2
(45) Date of Patent: Jul. 15, 2014

(54) ECM CONSTRUCTS FOR TISSUE REGENERATION

(71) Applicant: Francis Law Group, Alameda, CA (US)

(72) Inventor: Robert G. Matheny, Norcross, GA (US)

(73) Assignee: CorMatrix Cardiovascular, Inc., Roswell, GA (US)

( * ) Notice: Subject to any disclaimer, the term of this patent is extended or adjusted under 35 U.S.C. 154(b) by 35 days.

(21) Appl. No.: 13/686,131

(22) Filed: Nov. 27, 2012

(65) Prior Publication Data

US 2014/0148897 A1    May 29, 2014

(51) Int. Cl.
*A61F 2/02* (2006.01)
*A61F 2/06* (2013.01)

(52) U.S. Cl.
CPC .......................................... *A61F 2/06* (2013.01)
USPC .... 623/1.36; 623/1.41; 623/23.74; 623/23.76

(58) Field of Classification Search
USPC .......... 623/1.36, 1.41, 23.72–23.76; 606/151, 606/215
See application file for complete search history.

(56) References Cited

U.S. PATENT DOCUMENTS

| 7,560,036 | B2 * | 7/2009 | Golubovic-Liakopoulos et al. ................................ 216/2 |
| 7,686,842 | B2 * | 3/2010 | Pavcnik et al. ............... 623/1.13 |
| 8,337,537 | B2 * | 12/2012 | Pelo et al. ...................... 606/329 |
| 2003/0097173 | A1 * | 5/2003 | Dutta ............................ 623/1.38 |
| 2009/0125096 | A1 * | 5/2009 | Chu et al. ..................... 623/1.14 |

* cited by examiner

*Primary Examiner* — David Isabella
*Assistant Examiner* — Dinah Baria
(74) *Attorney, Agent, or Firm* — Francis Law Group

(57) ABSTRACT

An extracellular matrix (ECM) construct having a biodegradable support scaffold that includes a plurality of biodegradable microneedles that are capable of piercing tissue and anchoring therein, and at least a first layer of first ECM material disposed on the top surface of the support scaffold.

20 Claims, 8 Drawing Sheets

*FIG. 5A*
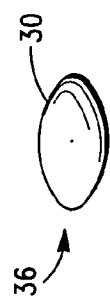
*FIG. 5B*
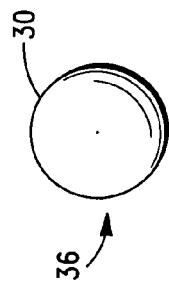
*FIG. 5C*
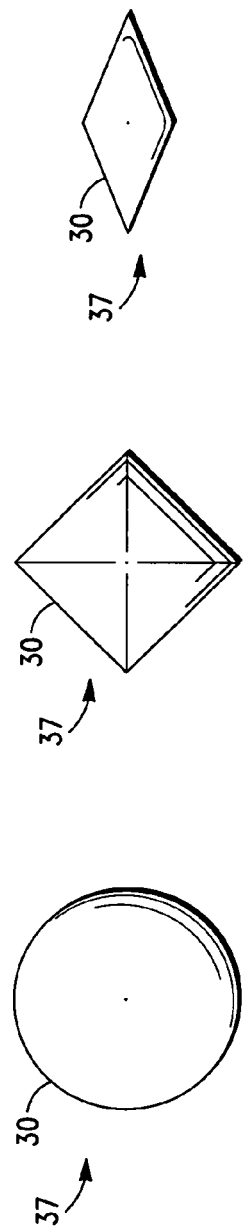
*FIG. 6A*
*FIG. 6B*
*FIG. 6C*
*FIG. 6D*

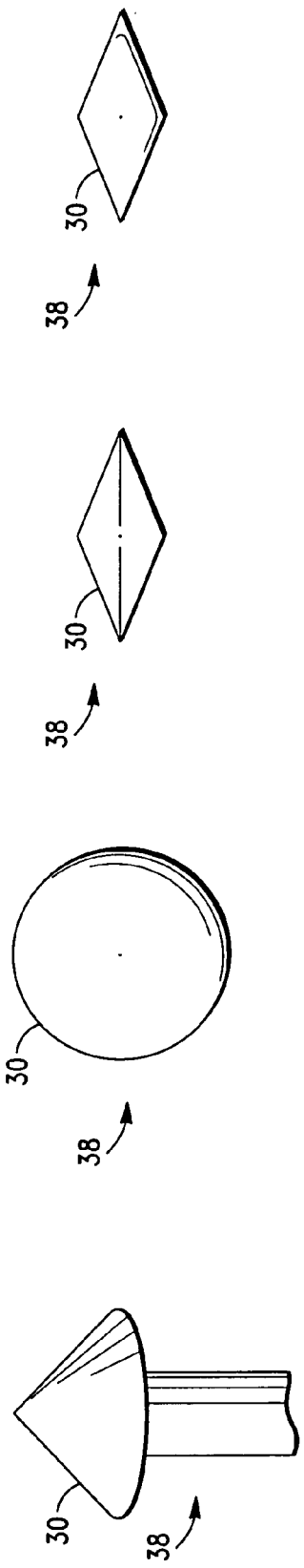
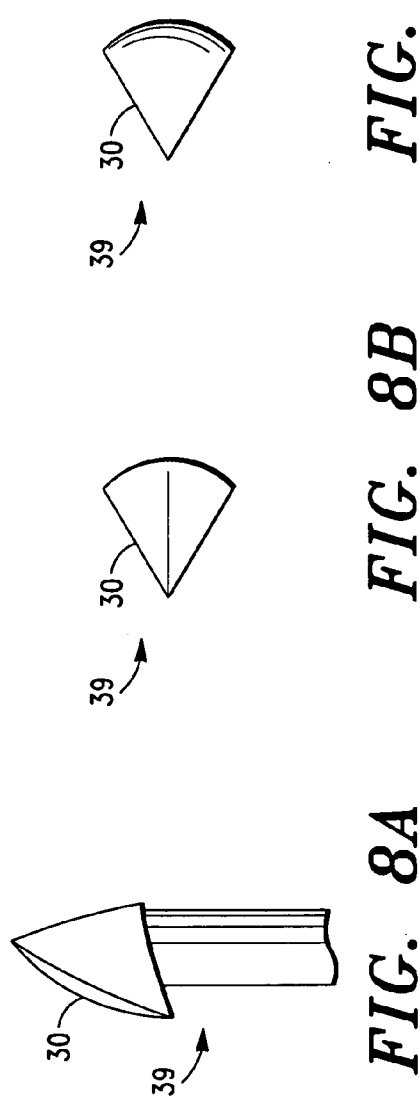

ECM CONSTRUCTS FOR TISSUE REGENERATION

FIELD OF THE INVENTION

The present invention relates to apparatus and methods for repairing tissue in mammals. More particularly, the present invention relates to extracellular matrix (ECM) constructs for repairing and/or regenerating tissue, and anchoring mechanisms for securing the constructs to tissue.

BACKGROUND OF THE INVENTION

As is well known in the art, various ECM based apparatus have been developed to regenerate tissue. Illustrative are the ECM based apparatus, i.e. grafts and endografts, disclosed in U.S. Pat. Nos. 7,795,027, 7,910,791, 7,905,826, and 8,025,896 and U.S. application Ser. No. 11/547,348.

The ECM material employed in the noted apparatus will, in most instances, induce host tissue proliferation, bioremodeling, and regeneration of tissue structures.

A major drawback of the noted ECM based apparatus, as well as most known apparatus, is that the means employed to secure the apparatus to tissue often comprise or include a permanent structure that remains in the body, i.e. non-biodegradable. As is well known in the art, such structures (or devices) can, and in most instances will, cause irritation and undesirable biologic responses in the surrounding tissue.

Such structures (and devices) are also prone to failure, resulting in severe adverse consequences, e.g., ruptured vessels.

A further drawback of known ECM apparatus is that the means employed to secure the apparatus to tissue is often ineffective. In the case of an ECM based endograft that is deployed in a cardiovascular vessel, if the endograft is not placed in intimate contact with the vessel wall, blood can, and in most instances will, pool between the endograft and vessel wall. The can result in severe adverse consequences, including vascular thrombosis.

There is thus a need for improved ECM devices or constructs that employ biocompatible and biodegradable securing means that effectively and safely secure the ECM constructs to tissue.

It is therefore an object of the present invention to provide ECM constructs that substantially reduce or eliminate the drawbacks and disadvantages associated with conventional ECM based apparatus.

It is another object of the present invention to provide ECM constructs that that employ biocompatible and biodegradable securing means that effectively and safely secure the ECM constructs to tissue.

It is another object of the present invention to provide. ECM constructs that can administer one or more pharmacological or therapeutic agents to a subject.

SUMMARY OF THE INVENTION

The present invention is directed to extracellular matrix (ECM) based constructs for regenerating tissue, and anchoring mechanisms for securing the apparatus to tissue.

In some embodiments of the invention, the ECM constructs include a biocompatible and biodegradable support scaffold, and at least one layer of ECM material disposed on the outer surface of the support scaffold.

In some embodiments, the ECM constructs include at least one layer of ECM material on the inner and outer surfaces of the support scaffold.

According to the invention, the ECM material can be derived from various mammalian tissue sources, including, without limitation, the small intestine, large intestine, stomach, lung, liver, kidney, pancreas, placenta, heart, bladder, prostate, tissue surrounding growing enamel, tissue surrounding growing bone, and any fetal tissue from any mammalian organ.

In some embodiments, the support scaffolds comprise a biodegradable metal selected from the group consisting of stainless steel and magnesium.

In some embodiments, the support scaffolds comprise an ECM material.

In some embodiments, the support scaffolds comprise a pharmacological composition.

In some embodiments, the support scaffolds comprise a biodegradable polymeric composition.

In some embodiments of the invention, the polymeric composition includes an ECM material.

In some embodiments, the polymeric composition includes a cell, such as, for example, a stem cell.

In some embodiments, the polymeric composition includes a protein, such as, for example, collagen.

In some embodiments, the polymeric composition includes a pharmacological agent or composition.

In some embodiments, the pharmacological composition comprises a bioactive agent that facilitates the process of tissue regeneration.

In some embodiments of the invention, the support scaffolds of the invention comprise a microneedle anchoring member having a plurality of biodegradable microneedles or barbs that are adapted to pierce tissue and secure the ECM constructs to the tissue.

In some embodiments, the microneedles comprise drug-eluting mechanisms that facilitate the direct administration of a pharmacological agent to engaged tissue.

According to the invention, upon placement of an ECM construct on target tissue, e.g., damaged or diseased region of the vessel, the ECM material will induce host tissue proliferation, bioremodeling, including neovascularization, and regeneration of tissue structures with site-specific structural and functional properties.

In some embodiments of the invention, wherein the support scaffold includes a pharmacological agent or the support scaffold includes drug-eluting microneedles, a desired biological and/or therapeutic action is also effectuated.

A key advantage of the ECM constructs of the invention is the provision of ECM constructs that include unique biodegradable microneedle anchoring members that effectively secure the ECM constructs to target tissue for a pre-determined period of time.

BRIEF DESCRIPTION OF THE DRAWINGS

Further features and advantages will become apparent from the following and more particular description of the preferred embodiments of the invention, as illustrated in the accompanying drawings, and in which like referenced characters generally refer to the same parts or elements throughout the views, and in which:

FIG. 5A is a perspective view of one embodiment of a microneedle, in accordance with the invention;

FIG. 5B is a top plan view of the microneedle shown in FIG. 5A, in accordance with the invention;

FIG. 5C is a top plan view of the microneedle shown in FIG. 5A having a substantially elliptical shaped head, in accordance with the invention;

FIG. 6A is a perspective view of another embodiment of a microneedle, in accordance with the invention;

FIG. 6B is a top plan view of the microneedle shown in FIG. 6A, in accordance with the invention;

FIG. 6C is a top plan view of the microneedle shown in FIG. 5A having one embodiment of a rectangular pyramid shaped head, in accordance with the invention;

FIG. 6D is a top plan view of the microneedle shown in FIG. 5A having another embodiment of a rectangular pyramid shaped head, in accordance with the invention;

FIG. 7A is a perspective view of another embodiment of a microneedle, in accordance with the invention;

FIG. 7B is a top plan view of the microneedle shown in FIG. 7A, in accordance with the invention;

FIG. 7C is a top plan view of the microneedle shown in FIG. 7A having one embodiment of a rectangular pyramid shaped head, in accordance with the invention;

FIG. 7D is a top plan view of the microneedle shown in FIG. 7A having another embodiment of a rectangular pyramid shaped head, in accordance with the invention;

FIG. 8A is a perspective view of another embodiment of a microneedle, in accordance with the invention;

FIG. 8B is a top plan view of the microneedle shown in FIG. 8A, in accordance with the invention;

FIG. 8C is a top plan view of the microneedle shown in FIG. 8A having another embodiment of a head region, in accordance with the invention;

DETAILED DESCRIPTION OF THE PREFERRED EMBODIMENT

Figure 1:
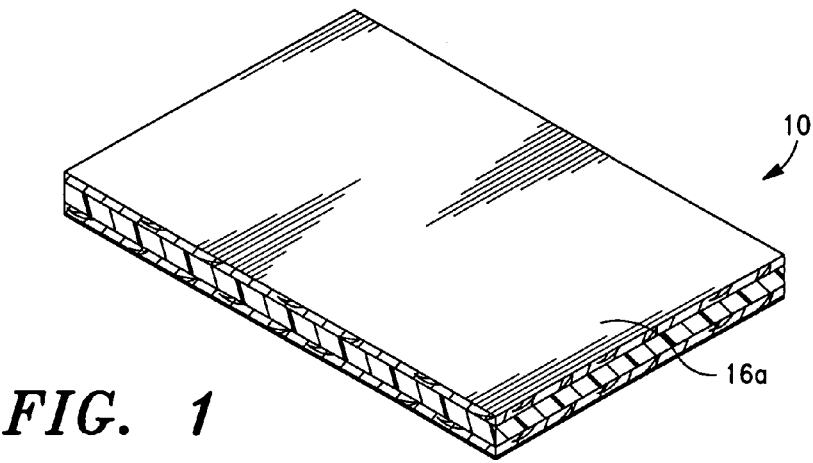
FIG. 1 is a perspective view of one embodiment of an ECM construct, in accordance with the invention.

Before describing the present invention in detail, it is to be understood that this invention is not limited to particularly exemplified apparatus, systems, structures or methods as such may, of course, vary. Thus, although a number of apparatus, systems and methods similar or equivalent to those described herein can be used in the practice of the present invention, the preferred apparatus, systems, structures and methods are described herein.

It is also to be understood that the terminology used herein is for the purpose of describing particular embodiments of the invention only and is not intended to be limiting.

Unless defined otherwise, all technical and scientific terms used herein have the same meaning as commonly understood by one having ordinary skill in the art to which the invention pertains.

Further, all publications, patents and patent applications cited herein, whether supra or infra, are hereby incorporated by reference in their entirety.

As used in this specification and the appended claims, the singular forms "a, "an" and "the" include plural referents unless the content clearly dictates otherwise. Thus, for example, reference to "an active" includes two or more such actives and the like.

Further, ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

It is also understood that there are a number of values disclosed herein, and that each value is also herein disclosed as "approximately" that particular value in addition to the value itself. For example, if the value "10" is disclosed, then "approximately 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed then "less than or equal to 10", as well as "greater than or equal to 10" is also disclosed.

DEFINITIONS

The term "graft", as used herein, means and includes a portion of a tissue or organ configured for placement on host tissue to repair and/or regenerate tissue.

The terms "endograft" and "prosthesis" are used interchangeably herein, and mean and include a device or system that is configured for implantation in a lumen or vessel, including, without limitation, stents, i.e. covered and non-covered, and other similar endoluminal support devices.

The term "vessel", as used herein, means and includes any bodily lumen, canal, conduit, duct or passageway, including, but not limited to, blood vessels, bile ducts, the esophagus, the trachea, the ureter and the urethra. A vessel can comprise an existing lumen, canal, conduit, duct or passageway or a lumen, canal, conduit, duct or passageway created by surgical intervention.

The term "extracellular matrix", as used herein, means a collagen-rich substance that is found in between cells in mammalian tissue and serves as a structural element in tissues. It typically comprises a complex mixture of polysaccharides and proteins secreted by cells. The extracellular matrix can be isolated and treated in a variety of ways. ECM material can be isolated from small intestine submucosa, stomach submucosa, urinary bladder submucosa, tissue mucosa, dura mater, liver basement membrane, pericardium or other tissues. Following isolation and treatment, it is commonly referred to as extracellular matrix or ECM material.

The term "biocompatible", as used herein, means a device or material that is substantially non-toxic in an in vivo environment, and is not substantially rejected by a recipient's physiological system, i.e. non-antigenic.

The terms "pharmacological agent", "pharmaceutical agent", "agent", "active agent", "drug", and "pharmaceutical composition" are used interchangeably herein, and mean and include an agent, drug, compound, composition of matter or mixture thereof, including its formulation, which provides some therapeutic, often beneficial, effect. This includes any physiologically or pharmacologically active substance that produces a localized or systemic effect or effects in animals, including warm blooded mammals, humans and primates; avians; domestic household or farm animals, such as cats, dogs, sheep, goats, cattle, horses and pigs; laboratory animals, such as mice, rats and guinea pigs; fish; reptiles; zoo and wild animals; and the like.

The terms "pharmacological agent", "pharmaceutical agent", "agent", "active agent", "drug", and "pharmaceutical composition" thus mean and include, without limitation, statins, antibiotics, anti-viral agents, analgesics, steroidal anti-inflammatories, non-steroidal anti-inflammatories, antineoplastics, anti-spasmodics, modulators of cell-extracellular matrix interactions, proteins, hormones, enzymes and enzyme inhibitors, anticoagulants and/or antithrombic agents, DNA, RNA, modified DNA and RNA, NSAIDs, inhibitors of DNA, RNA or protein synthesis, polypeptides, oligonucleotides, polynucleotides, nucleoproteins, compounds that modulate cell migration, compounds that modulate proliferation and growth of tissue, and vasodilating agents.

The terms "anti-inflammatory" and "anti-inflammatory agent" are also used interchangeably herein, and mean and include a "pharmacological agent" and/or "active agent formulation", which, when a therapeutically effective amount is administered to a subject, prevents or treats bodily tissue inflammation i.e. the protective tissue response to injury or destruction of tissues, which serves to destroy, dilute, or wall off both the injurious agent and the injured tissues. Anti-inflammatory agents thus include, without limitation, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, ciclofen, cintazone, cliprofen, clobetasol propionate, clobetasone butyrate, clopirac, cloticasone propionate, cormethasone acetate, cortodoxone, decanoate, deflazacort, delatestryl, depo-testosterone, desonide, desoximetasone, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, mesterolone, methandrostenolone, methenolone, methenolone acetate, methylprednisolone suleptanate, momiflumate, nabumetone, nandrolone, naproxen, naproxen sodium, naproxol, nimazone, olsalazine sodium, orgotein, orpanoxin, oxandrolane, oxaprozin, oxyphenbutazone, oxymetholone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, stanozolol, sudoxicam, sulindac, suprofen, talmetacin, talniflumate, talosalate, tebufelone, tenidap, tenidap sodium, tenoxicam, tesicam, tesimide, testosterone, testosterone blends, tetrydamine, tiopinac, tixocortol pivalate, tolmetin, tolmetin sodium, triclonide, triflumidate, zidometacin, and zomepirac sodium.

The terms "active agent formulation", "pharmacological agent formulation" and "agent formulation", are also used interchangeably herein, and mean and include an active agent optionally in combination with one or more pharmaceutically acceptable carriers and/or additional inert ingredients. According to the invention, the formulations can be either in solution or in suspension in the carrier.

The term "therapeutically effective", as used herein, means that the amount of the "pharmacological agent" and/or "active agent formulation" administered is of sufficient quantity to ameliorate one or more causes, symptoms, or sequelae of a disease or disorder. Such amelioration only requires a reduction or alteration, not necessarily elimination, of the cause, symptom, or sequelae of a disease or disorder.

The terms "prevent" and "preventing" are used interchangeably herein, and mean and include reducing the frequency or severity of a disease or condition. The term does not require an absolute preclusion of the disease or condition. Rather, this term includes decreasing the chance for disease occurrence.

The terms "treat" and "treatment" are used interchangeably herein, and mean and include medical management of a patient with the intent to cure, ameliorate, stabilize, or prevent a disease, pathological condition, or disorder. The terms include "active treatment", i.e. treatment directed specifically toward the improvement of a disease, pathological condition, or disorder, and "causal treatment", i.e. treatment directed toward removal of the cause of the associated disease, pathological condition, or disorder.

The terms "treat" and "treatment" further include "palliative treatment", i.e. treatment designed for the relief of symptoms rather than the curing of the disease, pathological condition, or disorder, "preventative treatment", i.e. treatment directed to minimizing or partially or completely inhibiting the development of the associated disease, pathological condition, or disorder, and "supportive treatment", i.e. treatment employed to supplement another specific therapy directed toward the improvement of the associated disease, pathological condition, or disorder.

The terms "optional" and "optionally" mean that the subsequently described event, circumstance, or material may or may not occur or be present, and that the description includes instances where the event, circumstance, or material occurs or is present and instances where it does not occur or is not present.

The term "comprise" and variations of the term, such as "comprising" and "comprises," means "including, but not limited to" and is not intended to exclude, for example, other additives, components, integers or steps.

The terms "subject" and "recipient" are used interchangeably herein, and mean and include any warm blooded mammal.

The following disclosure is provided to further explain in an enabling fashion the best modes of performing one or more embodiments of the present invention. The disclosure is further offered to enhance an understanding and appreciation for the inventive principles and advantages thereof, rather than to limit in any manner the invention. The invention is defined solely by the appended claims including any amendments made during the pendency of this application and all equivalents of those claims as issued.

As discussed above, the present invention is directed to extracellular matrix (ECM) constructs for repairing and/or regenerating tissue, and anchoring mechanisms for securing the constructs to tissue. As will readily be appreciated by one having ordinary skill in the art, the present invention substantially reduces or eliminates the disadvantages and drawbacks associated with prior art methods and apparatus for repairing damaged or diseased tissue.

In some embodiments, the ECM constructs of the invention comprise a planar or linear member, e.g., graft, having a biocompatible support scaffold, more preferably, a biocompatible and biodegradable support scaffold, and at least one layer of ECM material disposed on the outer surface of the support scaffold.

In some embodiments, the ECM constructs of the invention comprise a substantially tubular member.

In some embodiments, the ECM constructs include at least one layer of ECM material on the inner and outer surface of the support scaffold.

According to the invention, the ECM material can be derived from various mammalian tissue sources and methods for preparing same, such as disclosed in U.S. Pat. Nos. 7,550,004, 7,244,444, 6,379,710, 6,358,284, 6,206,931, 5,733,337 and 4,902,508 and U.S. application Ser. No. 12/707,427; which are incorporated by reference herein in their entirety. The mammalian tissue sources include, without limitation, the small intestine, large intestine, stomach, lung, liver, kidney, pancreas, placenta, heart, bladder, prostate, tissue surrounding growing enamel, tissue surrounding growing bone, and any fetal tissue from any mammalian organ.

As is well known in the art, the urinary bladder submucosa is an extracellular matrix that has the tunica mucosa (which includes the transitional epithelial layer and the tunica propria), a submucosal layer, three layers of muscularis, and the adventitia (a loose connective tissue layer). This general configuration is true also for small intestine submucosa (SIS) and stomach submucosa (SS).

Other tissues, such as the liver and pancreas have extracellular matrix called basement membrane. Basement membrane generally does not demonstrate the kind of tensile strength found in submucosa. However, other useful properties may be opportunistically employed from the extracellular matrices of such tissues as the liver, pancreas, placenta and lung tissues; all of which have either basement membrane for extracellular matrix or interstitial membrane (as with the lung). For example, pancreatic extracellular membrane supports beta islet cells that are critical to pancreatic function.

Also, for example, the liver is one tissue known to be able to regenerate itself and therefore special qualities may be present in the liver basement membrane that help facilitate that process. The extracellular matrices surrounding developing tooth enamel and developing bone also have particular advantages over other matrices in that they support the growth and differentiation of the hard tissues of bone and enamel.

According to the invention, matrices can be used in whole or in part, so that, for example, an extracellular matrix can contain just the basement membrane (or transitional epithelial layer) with the subadjacent tunica propria, the tunica submucosa, tunica muscularis, and tunica serosa. The extracellular matrix component of the composition can contain any or all of these layers, and thus could conceivably contain only the basement membrane portion, excluding the submucosa. However, generally, and especially since the submucosa is thought to contain and support the active growth factors and other proteins necessary for in vivo tissue regeneration, the matrix composition from any given source will contain the active extracellular matrix portions that support cell development and differentiation and tissue regeneration.

For purposes of this invention, the extracellular matrix from any of the mammalian tissue consists of several basically inseparable layers broadly termed extracellular matrix. For example, where it is thought that separating a basement membrane from the submucosa is considered to be very difficult, if not impossible, because the layers are thin and it is not possible to delaminate them from each other, the extracellular matrix from that particular layer will probably necessarily contain some basement membrane with the submucosa.

As stated above, the support scaffolds of the invention preferably comprise a biocompatible material, more preferably, a biocompatible and biodegradable material.

Thus, in some embodiments of the invention, the support scaffolds comprise a biodegradable metal.

In some embodiments, the biodegradable metal is selected from the group comprising, without limitation, stainless steel and magnesium.

In some embodiments of the invention, the metal support scaffolds include a coating of an immunomodulating compound that suppresses acute immune responses, while up regulating chronic immune response (i.e. tissue reconstruction).

In some embodiments, the immunomodulating compound comprises a polysaccharide, including without limitation, GAGs, dextrans, alginate and chitosan.

In some embodiments, immunomodulating compound comprises a polymeric material, including, without limitation, high molecular weight hyaluronic acid (HMW-HA).

In some embodiments, the support scaffolds comprise an ECM material.

In some embodiments, the support scaffolds comprise a pharmacological composition.

In some embodiments, the pharmacological composition comprises a pharmacological composition selected from the group comprising, without limitation, antibiotics, anti-viral agents, analgesics, steroidal anti-inflammatories, non-steroidal anti-inflammatories, anti-neoplastics, anti-spasmodics, modulators of cell-extracellular matrix interactions, proteins, hormones, enzymes and enzyme inhibitors, anticoagulants and/or antithrombic agents, DNA, RNA, modified DNA and RNA, NSAIDs, inhibitors of DNA, RNA or protein synthesis, polypeptides, oligonucleotides, polynucleotides, nucleoproteins, compounds that modulate cell migration, compounds that modulate proliferation and growth of tissue, and vasodilating agents.

In some embodiments, the support scaffolds comprise a biodegradable polymeric composition.

In some embodiments, the polymeric composition comprises a polymeric material selected from the group comprising, without limitation, polyglycolide (PGA), polylactide (PLA), polyepsilon-caprolactone, poly dioxanone (a polyether-ester), poly lactide-co-glycolide, polyamide esters, polyalkalene esters, polyvinyl esters, polyvinyl alcohol, and polyanhydrides. Natural polymeric materials, include, without limitation, polysaccharides (e.g. starch and cellulose), proteins (e.g., gelatin, casein, silk, wool, etc.), and polyesters (e.g., polyhydroxyalkanoates).

In some embodiments of the invention, the polymeric composition includes an ECM material.

In some embodiments of the invention, the polymeric composition includes a cell. According to the invention, the cell can comprise, without limitation, a stem cell, such as, for example, a human embryonic stem cell, fetal cell, fetal cardiomyocyte, myofibroblast, mesenchymal stem cell, autotransplanted expanded cardiomyocyte, adipocyte, totipotent cell, pluripotent cell, blood stem cell, myoblast, adult stem cell, bone marrow cell, mesenchymal cell, embryonic stem cell, parenchymal cell, epithelial cell, endothelial cell, mesothelial cell, fibroblast, myofibroblast, osteoblast, chondrocyte, exogenous cell, endogenous cell, stem cell, hematopoetic stem cell, pluripotent stem cell, bone marrow-derived progenitor cell, progenitor cell, myocardial cell, skeletal cell, undifferentiated cell, multi-potent progenitor cell, unipotent progenitor cell, monocyte, cardiomyocyte, cardiac myoblast, skeletal myoblast, macrophage, capillary endothelial cell, xenogenic cell, and allogenic cell.

In some embodiments of the invention, the polymeric composition includes a protein. According to the invention, the protein can comprise, without limitation, a growth factor, collagen, proteoglycan, glycosaminoglycan (GAG) chain, glycoprotein, cytokine, cell-surface associated protein, cell adhesion molecule (CAM), angiogenic growth factor, endothelial ligand, matrikine, matrix metalloprotease, cadherin, immunoglobin, fibril collagen, non-fibrillar collagen, basement membrane collagen, multiplexin, small-leucine rich proteoglycan, decorin, biglycan, fibromodulin, keratocan, lumican, epiphycan, heparan sulfate proteoglycan, perlecan, agrin, testican, syndecan, glypican, serglycin, selectin, lectican, aggrecan, versican, nuerocan, brevican, cytoplasmic domain-44 (CD44), macrophage stimulating factor, amyloid precursor protein, heparin, chondroitin sulfate B (dermatan sulfate), chondroitin sulfate A, heparan sulfate, hyaluronic acid, fibronectin (Fn), tenascin, elastin, fibrillin, laminin, nidogen/entactin, fibulin I, fibulin II, integrin, a transmembrane molecule, platelet derived growth factor (PDGF), epidermal growth factor (EGF), transforming growth factor alpha (TGF-alpha), transforming growth factor beta (TGF-beta), fibroblast growth factor-2 (FGF-2) (also called basic fibroblast growth factor (bFGF)), thrombospondin, osteopontin, angiotensin converting enzyme (ACE), and vascular epithelial growth factor (VEGF).

In some embodiments of the invention, the polymeric composition includes at least one of the aforementioned pharmacological agents or compositions.

In some embodiments of the invention, the polymeric composition comprises a bioactive that facilitates the process of tissue regeneration.

In some embodiments of the invention, wherein the support scaffolds comprise an ECM material, the ECM material includes at least one of the aforementioned pharmacological agents or compositions.

In a preferred embodiment of the invention, the support scaffolds of the invention are designed and adapted to degrade at a predetermined rate. Since the scaffolds of the invention are primarily designed to maintain contact of the ECM material to tissue until the remodeling and/or regeneration of new tissue, in some embodiments, the support scaffolds are preferably designed to degrade shortly after the commencement of new tissue growth.

As stated above, in some embodiments of the invention, the support scaffolds of the invention comprise a microneedle anchoring member having a plurality of biodegradable microneedles or barbs that are adapted to pierce tissue and secure the ECM constructs to tissue.

In some embodiments, the microneedles comprise drug-eluting members that facilitate the direct administration of a pharmacological agent or composition to tissue, e.g. host tissue of a vascular structure.

According to the invention, upon placement of an ECM construct on host tissue, e.g., damaged or diseased region of the vessel, the ECM material induces tissue proliferation, bioremodeling, including neovascularization, e.g., vasculogenesis, angiogenesis and intussusceptions, and regeneration of new tissue structures with site-specific structural and functional properties.

In some embodiments of the invention, wherein the support scaffold of the ECM construct includes a pharmacological agent or, as discussed in detail below, the support scaffold comprises a microneedle anchoring member having drug-eluting microneedles, a desired biological and/or therapeutic action is also effectuated.

Figure 2:
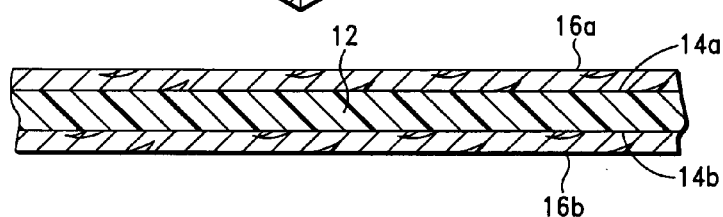
FIG. 2 is a front plan view of the ECM construct shown in FIG. 1, in accordance with the invention.

Referring now to FIGS. 1-2, there is shown one embodiment of an ECM construct of the invention (denoted generally "10"). Although the ECM construct 10 has a generally linear or flat shape, it is understood that the ECM construct 10 is not limited to a linear or flat shape. According to the invention, the ECM construct 10 can have various shapes, e.g. curved, to facilitate contact, preferably, substantially full contact with host tissue.

As illustrated in FIG. 1, the ECM construct 10 includes a support scaffold 12, at least a first layer of ECM material 16a disposed proximate or on the top surface 14a of the scaffold 12, and at least a second layer of ECM material 16b disposed proximate or on the bottom surface 14b of the scaffold 12. The support scaffold 12 is thus encased within the ECM layers 16a, 16b.

In some envisioned embodiments of the invention, the ECM construct 10 only includes the support scaffold 12 and at least a first layer of ECM material 16a disposed proximate or on the top surface 14a of the scaffold 12.

In some embodiments of the invention, first layer of ECM material 16a that is disposed proximate or on the top surface 14a of the scaffold 12 comprises a plurality of ECM sheets, i.e. a multi-layer ECM construct. In some embodiments of the invention, the first layer of ECM material 16b that is disposed proximate or on the bottom surface 14b of the scaffold 12 comprises a plurality of ECM sheets. In some embodiments of the invention, the first and second layers of ECM material 16a, 16b comprise a plurality of ECM sheets.

Figure 3:
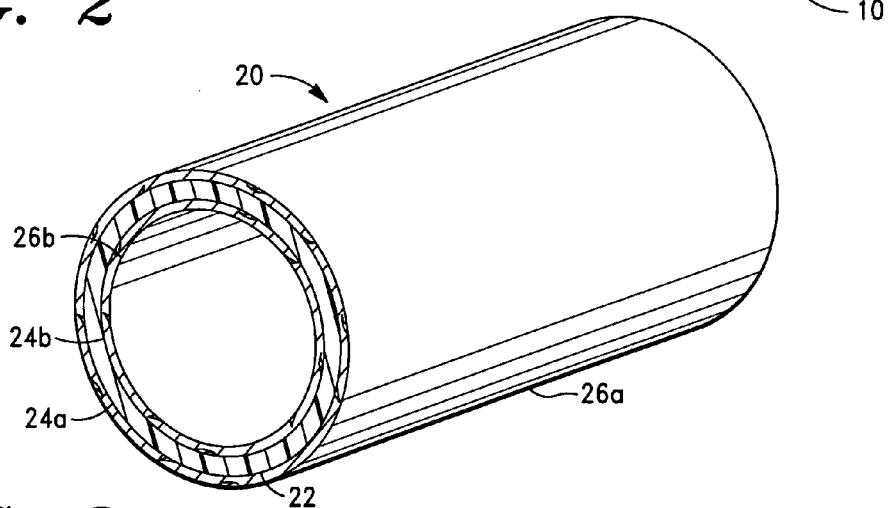
FIG. 3 is a perspective view of another embodiment of an ECM construct, in accordance with the invention.
Figure 4:
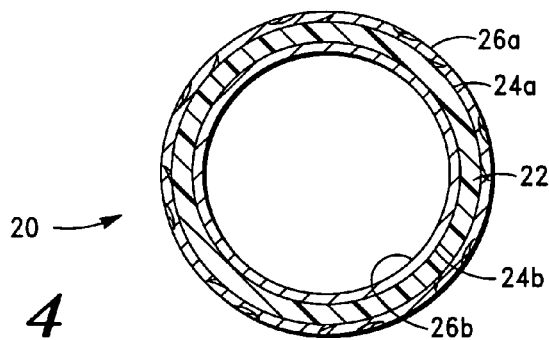
FIG. 4 is a front plan view of the ECM construct shown in FIG. 3, in accordance with the invention.

Referring now to FIGS. 3-4, there is shown one embodiment of an ECM construct of the invention. As illustrated in FIG. 4, in this embodiment, the ECM construct 20 comprises a tubular member, i.e. conduit.

The ECM construct 20 similarly includes a support scaffold 22, at least a first layer of ECM material 26a disposed proximate or on the top surface 24a of the scaffold 22, and at least a second layer of ECM material 26b disposed proximate or on the bottom surface 24b of the scaffold 22.

In some embodiments of the invention, the first or second layers of ECM material 26a, 26b comprise a plurality of wrapped ECM sheets. In some embodiments, the first and second layers of ECM material 26a, 26b comprise a plurality of ECM sheets.

According to the invention, the ECM material layers 16a, 16b and 26a, 26b can be secured to the supports scaffolds 12, 22 by any conventional means, e.g., laminating ends, stitching ends, etc.

In some embodiments of the invention, the ECM material layers 16a, 16b and 26a, 26b are stitched to the supports scaffolds 12, 22 using ECM thread.

As indicated above, in some embodiments of the invention, the support scaffolds of the invention comprise a microneedle anchoring member. In a preferred embodiment, the microneedle anchoring member includes at least one, more preferably, a plurality of biodegradable microneedles or barbs that are adapted to pierce tissue and secure the ECM constructs to tissue, e.g. host tissue of a vascular structure.

According to the invention, various shaped microneedles or barbs can be employed within the scope of the invention; provided, the microneedle or barb has a head (or head region) that is able to pierce tissue and maintain engaged to the tissue for a predetermined period of time.

In some embodiments of the invention, the biodegradable microneedles are adapted to secure an ECM construct to tissue for a predetermined engagement period of time within the process of new tissue regeneration.

In some embodiments of the invention, the predetermined engagement period of time is within the range of approximately 12-36 months. In some embodiments, the engagement period of time is within the range of approximately 3-12 months. In some embodiments, the engagement period of time is within the range of approximately 1-3 months.

Thus, in some embodiments, when an ECM construct of the invention is deployed in a vessel, the microneedles remain engaged to the host tissue of the vessel (or vessel wall) long enough to allow blood vessels to begin to grow. Once blood vessels begin to grow into the ECM material disposed on the support scaffold and stem cells attach to the surface, an endothelium surface grows across the ECM construct and starts to remodel into healthy, native vascular wall cells and, thereby, creating a remodeled, natural vascular wall.

Referring now to FIGS. 5A-5C, 6A-6D, 7A-7D and 8A-8C, there are shown several embodiments of suitable tissue piercing microneedles that can be employed within the scope of the invention. It is understood that the microneedles shown in FIGS. 5A-5C, 6A-6D, 7A-7D and 8A-8C are merely exemplar microneedles that can be employed within the scope of the invention and, hence, do not limit the scope of the invention in any manner. Indeed, as stated above, various other shaped microneedles can be employed within the scope of the invention; provided, the microneedle has a head (or head region) that is able to pierce tissue and maintain engaged to the tissue for a predetermined period of time.

As illustrated in FIGS. 5A-5C, 6A-6D, 7A-7D, and 8A-8C, each microneedle of the invention, including microneedles 36, 37, 38 and 39, includes a head or head region 30, a shaft 32 and base 34.

Referring first to FIGS. 5A-5C, there is shown one embodiment of a microneedle of the invention (denoted "36"). As illustrated in FIGS. 5A-5B, in some embodiments of the invention, the microneedle 36 has a conventional tapered, i.e. round pointed, end or head region 30. As illustrated in FIG. 5C, in some embodiments, the microneedle 36 has a pointed elliptical shaped head region 30.

Referring now to FIGS. 6A-5D, there is shown another embodiment of a microneedle of the invention (denoted "37"). As illustrated in FIGS. 6A-6B, in some embodiments of the invention, the microneedle 37 has a round (or circular) pointed head region 30 that is adapted to pierce tissue. As illustrated in FIGS. 6C and 6D, in some embodiments, the microneedle 37 has a pointed rectangular pyramid shaped head region 30.

Referring now to FIGS. 7A-7D, there is shown another embodiment of a microneedle of the invention (denoted "38"). As illustrated in FIGS. 6A-6B, in some embodiments of the invention, the microneedle 38 has a round pointed head region 30. As illustrated in FIGS. 6C and 6D, in some embodiments, the microneedle 37 has a pointed rectangular pyramid shaped head region 30.

Referring now to FIGS. 8A-8C, there is shown another embodiment of a microneedle of the invention (denoted "39"). As illustrated in FIGS. 8A-8B, in some embodiments of the invention, the microneedle 39 has a pointed half-arrow shaped head region 30. As illustrated in FIG. 8C, in some embodiments, the microneedle 39 has a rounded half-arrow shaped head region 30.

In some embodiments, the microneedles of the invention comprise drug-eluting members, i.e. structures that facilitate the direct administration of a pharmacological agent or composition to tissue.

According to the invention, the pharmacological composition can comprise, without limitation, antibiotics, anti-viral agents, analgesics, steroidal anti-inflammatories, non-steroidal anti-inflammatories, anti-neoplastics, anti-spasmodics, modulators of cell-extracellular matrix interactions, proteins, hormones, enzymes and enzyme inhibitors, anticoagulants and/or antithrombic agents, DNA, RNA, modified DNA and RNA, NSAIDs, inhibitors of DNA, RNA or protein synthesis, polypeptides, oligonucleotides, polynucleotides, nucleoproteins, compounds that modulate cell migration, compounds that modulate proliferation and growth of tissue, and vasodilating agents.

According to the invention, the pharmacological composition can also include a statin. Suitable statins include, without limitation, atorvastatin, cerivastatin, fluvastatin, lovastatin, mevastatin, pitavastatin, pravastatin, rosuvastatin, and simvastatin.

In some embodiments of the invention, the drug-eluting capability is facilitated by forming the microneedle(s) out of a pharmacological composition, whereby upon engagement of a biodegradable microneedle to a recipient's tissue, the microneedle dissolves or degrades and the pharmacological composition is administered to the recipient at the engagement site.

In some embodiments, the drug-eluting capability is facilitated by coating the microneedle(s) with a pharmacological composition, whereby upon engagement of a microneedle to a recipient's tissue, the pharmacological composition is absorbed and, hence, administered to the recipient at the engagement site.

Figure 9:
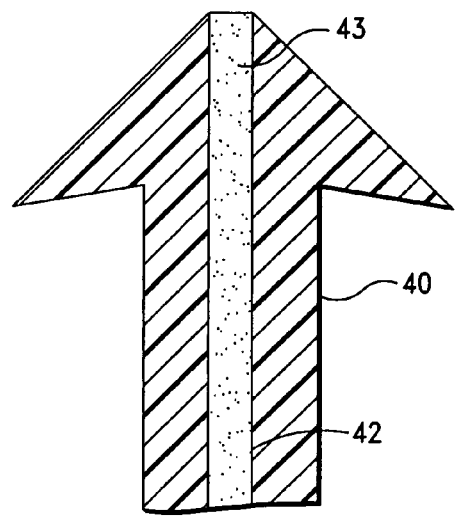
FIG. 9 is a side plan view of one embodiment of a drug-eluting microneedle, in accordance with the invention.

In some embodiments of the invention, the drug-eluting capability is facilitated by providing the microneedle(s) with an internal reservoir that is adapted to receive and contain a pharmacological composition therein. Referring now to FIG. 9, there is shown one embodiment of a microneedle 40 having an internal reservoir 42 that is adapted to receive and contain a pharmacological composition 43. According to the invention, upon engagement of the biodegradable microneedle 40 to a recipient's tissue, the microneedle 40 dissolves or degrades and the pharmacological composition contained in the reservoir 42 is administered to the recipient at the engagement site.

Figure 10:
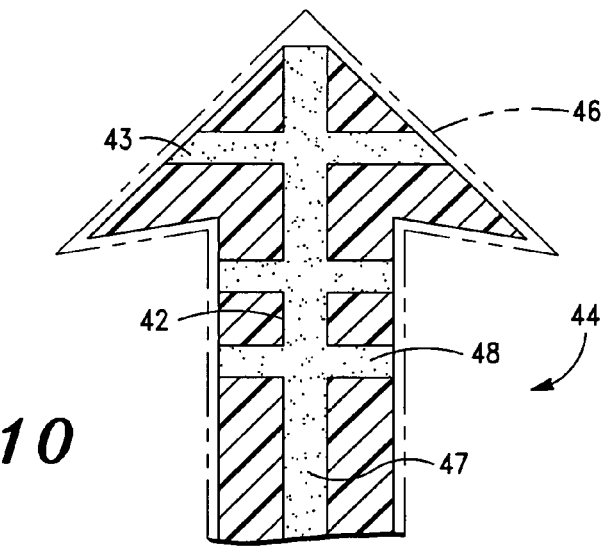
FIG. 10 is a side plan view of another embodiment of a drug-eluting microneedle, in accordance with the invention.

Referring now to FIG. 10, in some embodiments of the invention, the microneedle 44 has an internal reservoir 47 that is similarly adapted to receive and contain a pharmacological composition 43. However, in this embodiment, the microneedle 44 also includes at least one, more preferably, a plurality of lumens 48 in communication with the reservoir 47 and, hence, pharmaceutical composition 43 contained therein.

Figure 11:
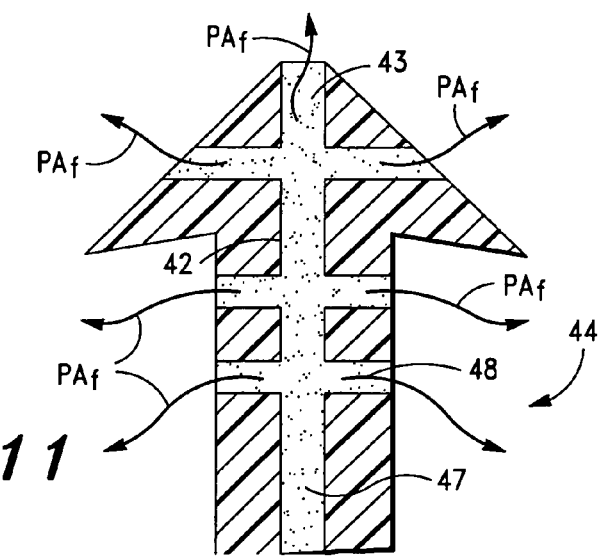
FIG. 11 is a side plan view of the microneedle shown in FIG. 10, showing the outward flow of a contained pharmaceutical after degradation of the exterior coating, in accordance with the invention.

As illustrated in FIG. 11, the microneedle 44 further includes a biodegradable or bioabsorbable coating (or sealing layer) 46 on the outer surface to temporarily seal the reservoir 47 and inter-connected lumens 48. According to the invention, upon engagement of the microneedle 44 to a recipient's tissue, the coating 46 dissolves or degrades and the pharmacological composition 43 contained in the reservoir 42 flows out of the lumens 48 (denoted by Arrows $PA_f$ in FIG. 11) and is administered to the recipient at the engagement site.

According to the invention, the microneedle coating 46 can comprise any bioabsorbable material or compound, including, various known enteric polymers, such as cellulose, vinyl and acrylic derivatives. Suitable bioabsorbable materials thus include, without limitation, cellulose acetate phthalate (CAP) and polyvinyl acetate phthalate (PVAP).

According to the invention, the on-set and administration rate of a pharmacological composition from a microneedle of the invention can be determined and regulated by, among other things, the composition and/or properties of the base microneedle, e.g. dissolution rate, size of lumens, etc., and the composition and/or properties of the pharmacological composition and sealing coatings.

Figure 12A:
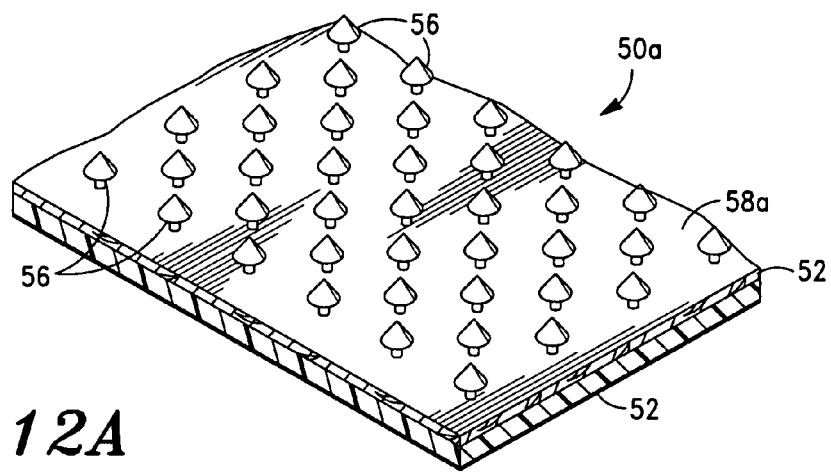
FIG. 12A is a perspective view of one embodiment of an ECM construct having a microneedle securing member, in accordance with the invention.
Figure 12B:
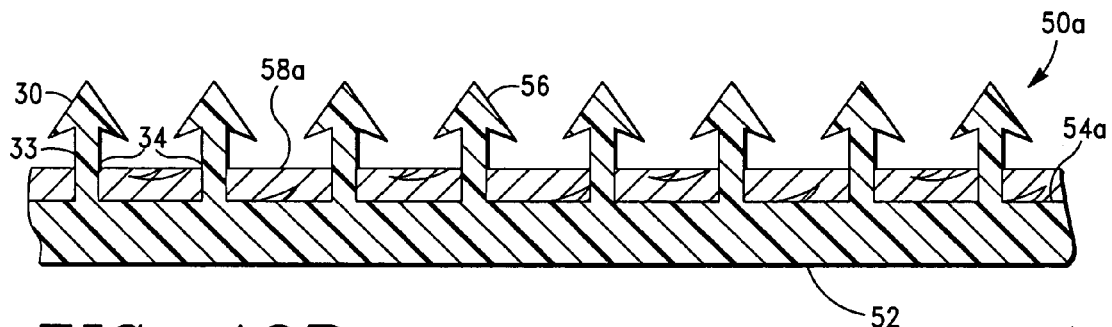
FIG. 12B is a partial side, sectional plan view of the ECM construct shown in FIG. 12A, in accordance with the invention.
Figure 12C:
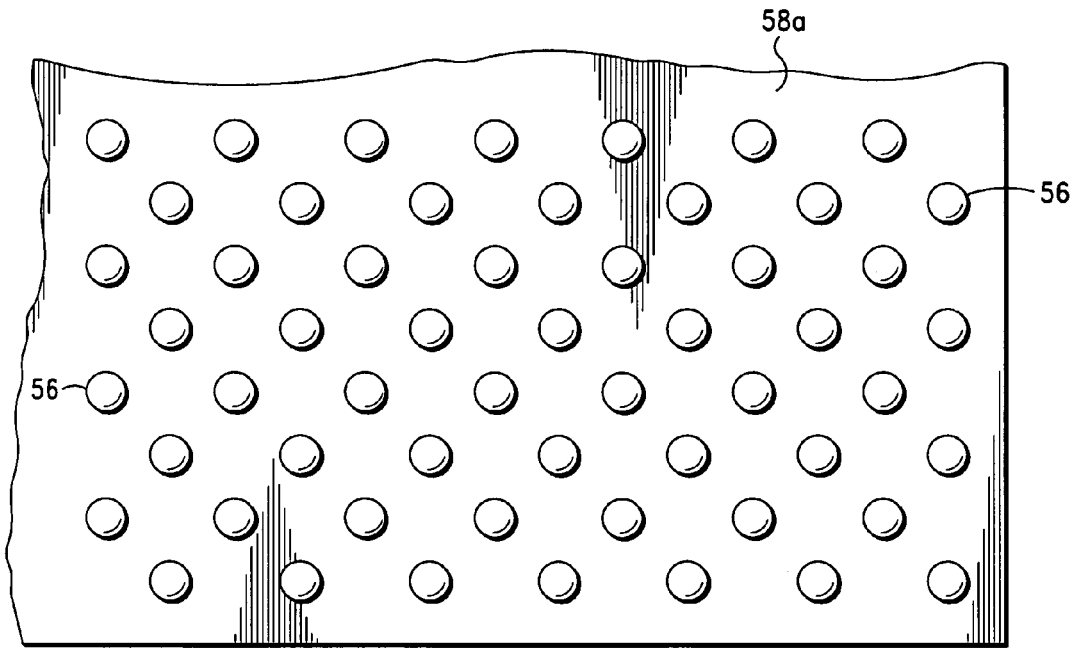
FIG. 12C is a top plan view of the ECM construct shown in FIG. 12A, in accordance with the invention.

Referring now to FIGS. 12A-12C, there is shown one embodiment of an ECM construct 50a of the invention having a microneedle anchoring mechanism or support scaffold 52 and an ECM layer 58a disposed proximate or on the top surface 54a of the scaffold 52. As illustrated in FIGS. 12A and 12B, the support scaffold 52 includes a plurality of microneedles 56, which preferably extend through and project out of the ECM layer 58a.

According to the invention, the support scaffold 52 can include any number of microneedles 56. The microneedles 56 can also comprise any of the aforementioned biocompatible materials and shapes illustrated in FIGS. 5A-5C, 6A-6D, 7A-7D and 8A-8C.

In some embodiments of the invention, the microneedles 56 comprise drug-eluting microneedles, as described above.

Figure 13A:
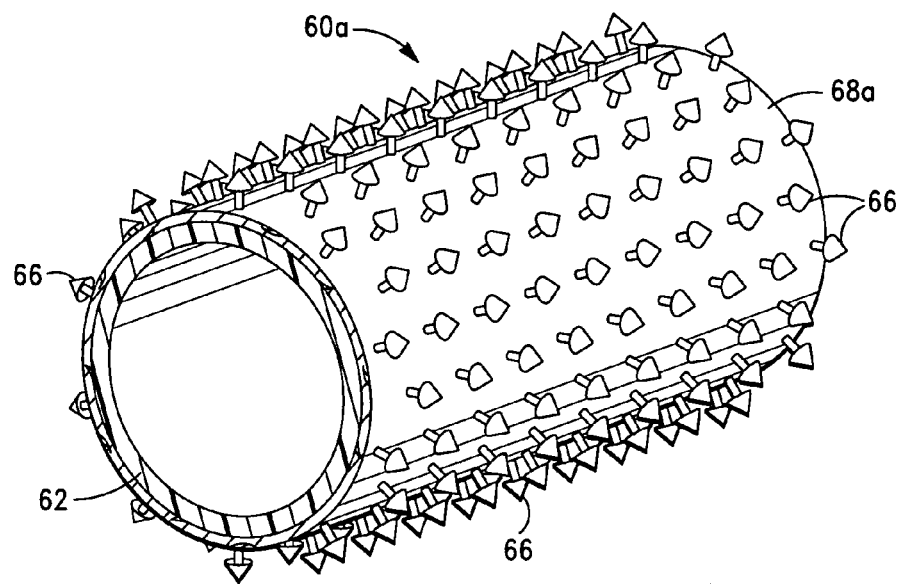
FIG. 13A is a perspective view of another embodiment of an ECM construct having a microneedle securing member, in accordance with the invention.
Figure 13B:
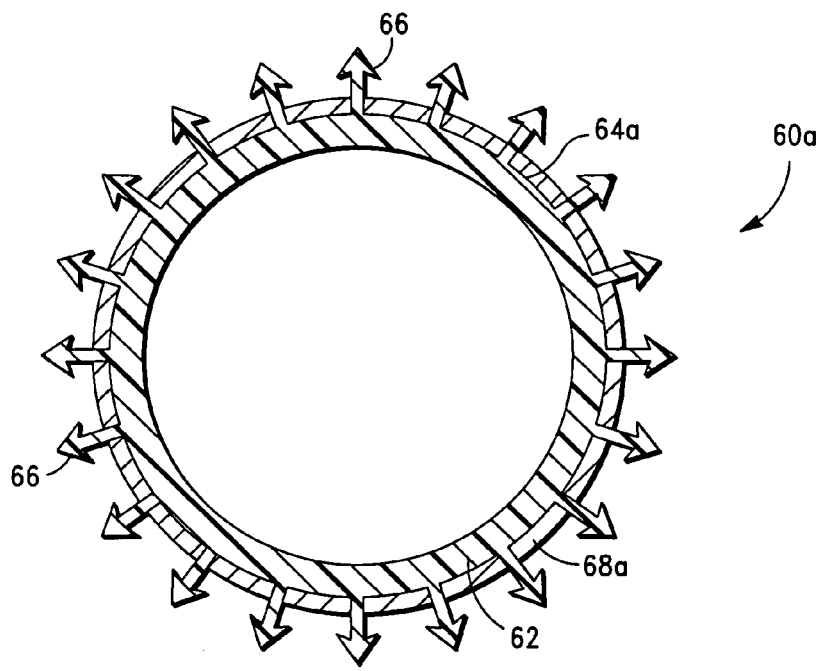
FIG. 13B is a front (or end) plan, sectional view of the ECM construct shown in FIG. 13A, in accordance with the invention.

Referring now to FIGS. 13A-13B, there is another embodiment of an ECM construct 60a of the invention that similarly includes a microneedle anchoring mechanism or support scaffold 62 and an ECM layer 68a disposed proximate or on the top surface 64a of the scaffold 62. The support scaffold 62 similarly includes a plurality of microneedles 66 that preferably extend through and project out of the ECM layer 68a.

As illustrated in FIGS. 13A-13B, in this embodiment, the ECM construct 60a has a tubular shape, i.e. conduit, to facilitate deployment in a lumen or vessel in the body, e.g., a cardiovascular vessel.

According to the invention, the ECM layers 58a, 68a can similarly comprise single or multiple sheets of ECM material.

Figure 14:
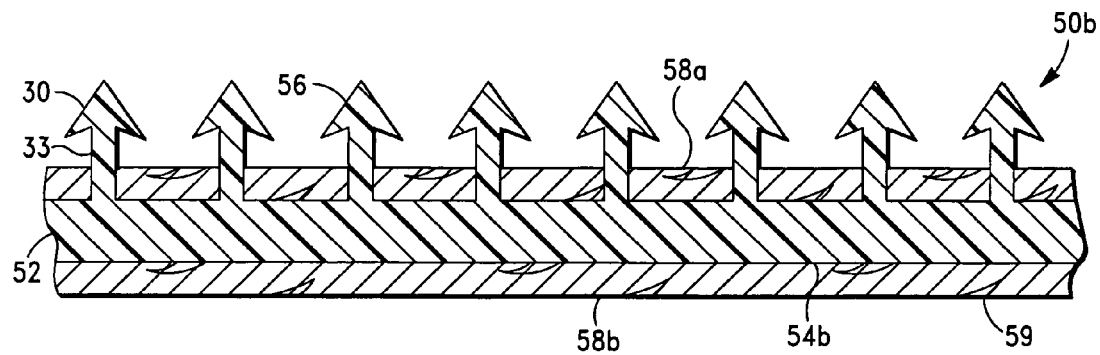
FIG. 14 is a partial side, sectional plan view of another embodiment of an ECM construct, in accordance with the invention.
Figure 15:
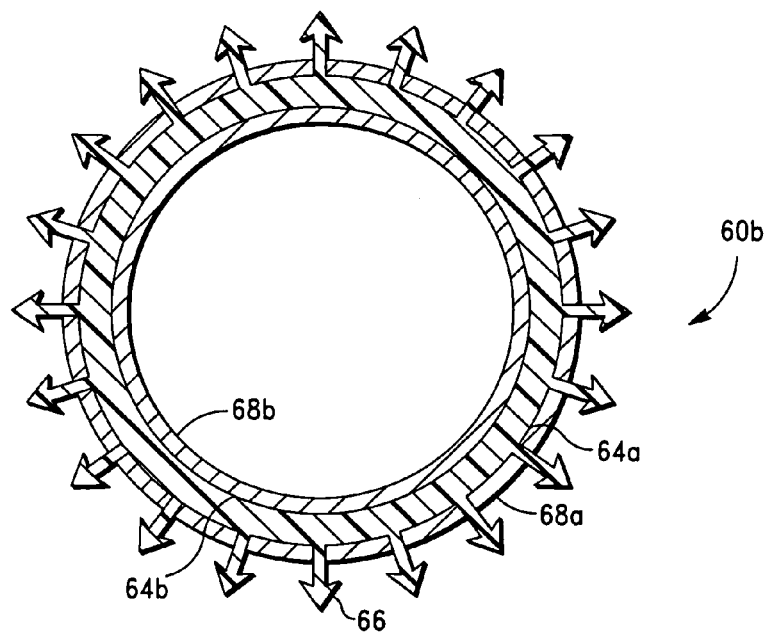
FIG. 15 is a front, sectional plan view of another embodiment of an ECM construct, in accordance with the invention.

Referring now to FIGS. 14 and 15, in some embodiments of the invention, the ECM constructs 50a, 60a include a second layer of ECM material. Referring first to FIG. 14, ECM construct 50b includes a second ECM layer 54b that is disposed proximate to or on the bottom surface 54b of the scaffold 52.

Referring now to FIG. 15, ECM construct 60b includes a second ECM layer 68b that is disposed proximate or on the bottom surface 64b of the scaffold 62.

According to the invention, the ECM layers 58b, 68b can similarly comprise single or multiple sheets of ECM material.

Figure 16:
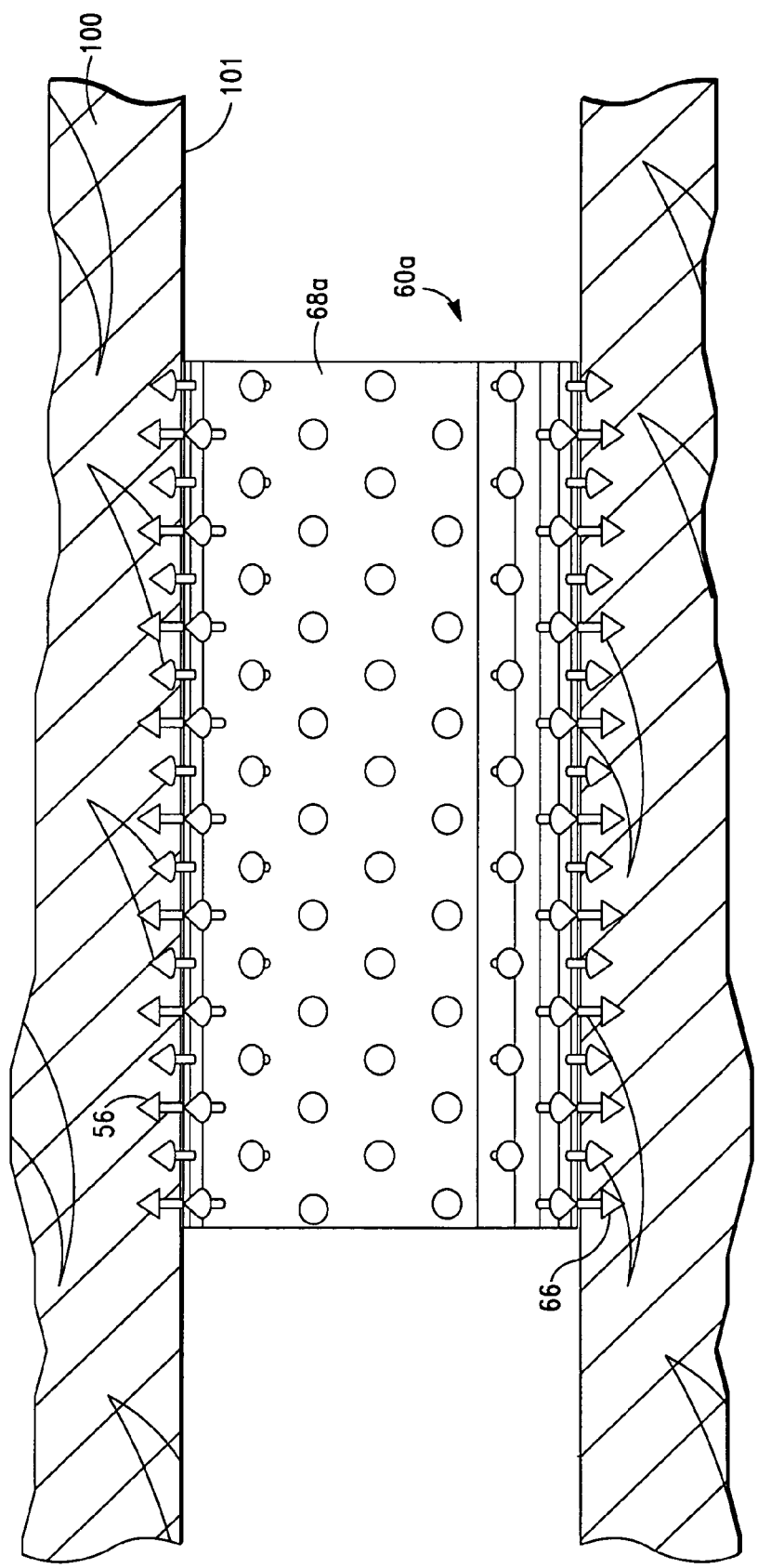
FIG. 16 is a side plan, partial sectional view of the ECM prosthesis shown in FIG. 15 engaged to tissue in a cardiovascular vessel, in accordance with the invention.

Referring now to FIG. 16, there is shown an illustration of ECM prosthesis 60a engaged to tissue in a cardiovascular vessel 100. According to the invention, when the prosthesis 60a is deployed in a vessel the microneedles 56 pierce the vessel 100 and secure the prosthesis 60a to the vessel tissue, and, hence, vessel wall 101.

As indicated above, upon placement of an ECM construct on host tissue, e.g., damaged or diseased region of the vessel, the ECM material induces tissue proliferation, bioremodeling, and regeneration of new tissue structures with site-specific structural and functional properties.

As also indicated above, when the ECM construct includes a support scaffold of the invention that includes a pharmacological agent or the support scaffold comprises a microneedle anchoring member having drug-eluting microneedles, a desired biological and/or therapeutic action is also effectuated.

One having ordinary skill in the art will thus readily appreciate that the ECM constructs of the invention provide numerous advantages over conventional ECM based and non-ECM based apparatus for repairing and/or regenerating tissue. Among the advantages are the following:

The provision of ECM constructs that induce host tissue proliferation, bioremodeling and regeneration of new tissue, and tissue structures with site-specific structural and functional properties;

The provision of ECM constructs that substantially reduce or eliminate (i) the harsh biological responses associated with conventional polymeric and metal ECM based and non-ECM apparatus, and (ii) the formation of inflammation and infection after deployment;

The provision of ECM constructs that employ biocompatible and biodegradable securing means that effectively and safely secure the ECM constructs to tissue for a predetermined period of time; and The provision of ECM constructs that effectively administer at least one pharmacological agent or composition to a subject's tissue and, thereby produce a desired biological and/or therapeutic effect.

As will also readily be appreciated by one having ordinary skill in the art, the ECM constructs can be readily employed in various medical procedures. The medical procedures include, without limitation, treatment of coronary and peripheral vascular disease (PVD) in cardiovascular vessels, including, but not limited to, iliacs, superficial femoral artery, renal artery, tibial artery, popliteal artery, etc., deep vein thromboses (DVT), vascular bypasses, and coronary vascular repair.

The scaffolds and/or microneedles of the invention can also be readily incorporated in or employed with various cardiovascular conduits, valves and grafts, including, without limitation, the heart valves and conduits disclosed in U.S. Pat. No. 7,998,196 and U.S. application Ser. No. 13/480,347, filed 24 May 2012, entitled "Extracellular Matrix Material Conduits and Methods of Making and Using Same" and Ser. No. 13/480,324, filed 24 May 2012, entitled "Extracellular Matrix Material Valve Conduit and Methods of Making Thereof".

The scaffolds and/or microneedles of the invention can also be employed with various additional vascular prostheses, including covered and non-covered stents.

It is understood that the noted applications of the ECM prostheses are merely exemplary and, thus, do not limit the scope of the possible applications and, hence, invention.

Without departing from the spirit and scope of this invention, one of ordinary skill can make various changes and modifications to the invention to adapt it to various usages and conditions. As such, these changes and modifications are properly, equitably, and intended to be, within the full range of equivalence of any issued claims.

What is claimed is:

1. An extracellular matrix (ECM) construct, comprising:
a biodegradable microneedle anchoring member having top and bottom surfaces and first and second ends, said microneedle anchoring member including a plurality of biodegradable microneedles that are capable of piercing tissue and anchoring therein, said plurality of biodegradable microneedles projecting from said microneedle anchoring member top surface from said first end to said second end, said microneedle anchoring member comprising a first ECM material; and
at least a first biodegradable layer comprising a second ECM material, said first biodegradable layer being disposed on said top surface of said microneedle anchoring member, said microneedle anchoring member being configured to secure said ECM construct to host tissue for a first engagement period of time in the range of 12-36 months, wherein, after said first engagement period of time said ECM construct is remodeled by said host tissue.

2. The ECM construct of claim 1, wherein said microneedle anchoring member includes a second biodegradable layer comprising a third ECM material.

3. The ECM construct of claim 2, wherein said second biodegradable layer is disposed on said first biodegradable layer.

4. The ECM construct of claim 2, wherein said second biodegradable layer is disposed on said bottom surface of said microneedle anchoring member.

5. The ECM construct of claim 2, wherein said third ECM material is derived from a third tissue source selected from the group consisting of the small intestine, large intestine, stomach, lung, liver, kidney, pancreas, placenta, heart, bladder, prostate, tissue surrounding growing enamel, tissue surrounding growing bone, and fetal tissue of a mammalian organ.

6. The ECM construct of claim 1, wherein said first ECM material is derived from a first tissue source selected from the group consisting of the small intestine, large intestine, stomach, lung, liver, kidney, pancreas, placenta, heart, bladder, prostate, tissue surrounding growing enamel, tissue surrounding growing bone, and fetal tissue of a mammalian organ.

7. The ECM construct of claim 1, wherein said second ECM material is derived from a second tissue source selected from the group consisting of the small intestine, large intestine, stomach, lung, liver, kidney, pancreas, placenta, heart, bladder, prostate, tissue surrounding growing enamel, tissue surrounding growing bone, and fetal tissue of a mammalian organ.

8. The ECM construct of claim 1, wherein said microneedles include an internal reservoir that is configured to receive a pharmaceutical composition therein.

9. The ECM construct of claim 8, wherein said microneedles include an outer biodegradable polymeric coating.

10. The ECM construct of claim 1, wherein said construct has a planar shape.

11. The ECM construct of claim 1, wherein said construct comprises a tubular member having a conduit therethrough.

12. The ECM construct of claim 1, wherein said tissue comprises host tissue of a vascular structure.

13. A biodegradable construct, comprising:
a biodegradable microneedle anchoring member having top and bottom surfaces and first and second ends, said microneedle anchoring member including a plurality of biodegradable microneedles that are capable of piercing tissue and anchoring therein, said plurality of biodegradable microneedles projecting from said microneedle anchoring member top surface from said first end to said second end, said microneedle anchoring member comprising a biodegradable polymeric material selected from the group consisting of polyglycolide (PGA), polylactide (PLA), polyepsilon-caprolactone, poly dioxanone (a polyether-ester), poly lactide-co-glycolide, polyamide esters, polyalkalene esters, polyvinyl esters, polyvinyl alcohol, and polyanhydrides; and
at least a first biodegradable layer comprising a first ECM material, said first biodegradable layer being disposed on said top surface of said microneedle anchoring member.

14. The ECM construct of claim 13, wherein said first ECM material is derived from a first tissue source selected from the group consisting of the small intestine, large intestine, stomach, lung, liver, kidney, pancreas, placenta, heart, bladder, prostate, tissue surrounding growing enamel, tissue surrounding growing bone, and fetal tissue of a mammalian organ.

15. The ECM construct of claim 13, wherein said biodegradable polymeric material further comprises a cell selected from the group consisting of a human embryonic stem cell, fetal cell, fetal cardiomyocyte, myofibroblast, mesenchymal stem cell, autotransplanted expanded cardiomyocyte, adipocyte, totipotent cell, blood stem cell, adult stem cell, bone marrow cell, embryonic stem cell, parenchymal cell, epithelial cell, endothelial cell, mesothelial cell, fibroblast, myofibroblast, osteoblast, chondrocyte, exogenous cell, endogenous cell, stem cell, hematopoetic stem cell, pluripotent stem cell, progenitor cell, myocardial cell, skeletal cell, multi-potent progenitor cell, unipotent progenitor cell, monocyte, cardiomyocyte, cardiac myoblast, skeletal myoblast, macrophage, capillary endothelial cell, xenogenic cell and allogenic cell.

16. The ECM construct of claim 13, wherein said biodegradable polymeric material further comprises a protein selected from the group consisting of collagen, proteoglycan, glycosaminoglycan (GAG) chain, glycoprotein, cytokine, cell-surface associated protein, cell adhesion molecule (CAM), angiogenic growth factor, endothelial ligand, matrikine, matrix metalloprotease, cadherin, immunoglobin, fibril collagen, non-fibrillar collagen, basement membrane collagen, multiplexin, small-leucine rich proteoglycan, decorin, biglycan, fibromodulin, keratocan, lumican, epiphycan, heparan sulfate proteoglycan, perlecan, agrin, testican, syndecan, glypican, serglycin, selectin, lectican, aggrecan, versican, nuerocan, brevican, cytoplasmic domain-44 (CD44), macrophage stimulating factor, amyloid precursor protein, heparin, chondroitin sulfate B (dermatan sulfate), chondroitin sulfate A, heparan sulfate, hyaluronic acid, fibronectin (Fn), tenascin, elastin, fibrillin, laminin, nidogen/entactin, fibulin I, fibulin II, integrin, a transmembrane molecule, platelet derived growth factor (PDGF), epidermal growth factor (EGF), transforming growth factor alpha (TGF-alpha), transforming growth factor beta (TGF-beta), fibroblast growth factor-2 (FGF-2) (also called basic fibroblast growth factor (bFGF)), thrombospondin, osteopontin, angiotensin converting enzyme (ACE), and vascular epithelial growth factor (VEGF).

17. A biodegradable construct, comprising:
- a biodegradable microneedle anchoring member having top and bottom surfaces and first and second ends, said microneedle anchoring member including a plurality of biodegradable microneedles that are capable of piercing tissue and anchoring therein, said plurality of biodegradable microneedles projecting from said microneedle anchoring member top surface from said first end to said second end, said microneedle anchoring member comprising a pharmacological composition; and
- at least a first biodegradable layer comprising a first ECM material, said first biodegradable layer being disposed on said top surface of said microneedle anchoring member.

18. The ECM construct of claim 17, wherein said pharmacological composition comprises a pharmacological composition selected from the group consisting of antibiotics, anti-viral agents, analgesics, steroidal anti-inflammatories, non-steroidal anti-inflammatories, anti-neoplastics, anti-spasmodics, modulators of cell-extracellular matrix interactions, proteins, hormones, enzymes and enzyme inhibitors, anticoagulants and/or antithrombic agents, DNA, RNA, modified DNA and RNA, NSAIDs, inhibitors of DNA, RNA or protein synthesis, polypeptides, oligonucleotides, polynucleotides, nucleoproteins, compounds modulating cell migration, compounds modulating proliferation and growth of tissue, and vasodilating agents.

19. A biodegradable construct, comprising:
- a biodegradable microneedle anchoring member having top and bottom surfaces and first and second ends, said microneedle anchoring member including a plurality of biodegradable microneedles that are capable of piercing tissue and anchoring therein, said plurality of biodegradable microneedles projecting from said microneedle anchoring member top surface from said first end to said second end, said microneedle anchoring member comprising a biodegradable metal selected from the group consisting of stainless steel and magnesium; and
- at least a first biodegradable layer comprising a first ECM material, said first biodegradable layer being disposed on said top surface of said microneedle anchoring member.

20. The biodegradable construct of claim 19, wherein said first ECM material is derived from a first tissue source selected from the group consisting of the small intestine, large intestine, stomach, lung, liver, kidney, pancreas, placenta, heart, bladder, prostate, tissue surrounding growing enamel, tissue surrounding growing bone, and fetal tissue of a mammalian organ.

* * * * *